United States Patent [19]

Engelbrecht et al.

[11] Patent Number: 4,645,507
[45] Date of Patent: Feb. 24, 1987

[54] PROSTHESIS

[75] Inventors: Eckart Engelbrecht, Hamburg; Elmar Nieder, Jork; Arnold Keller, Kaihude, all of Fed. Rep. of Germany

[73] Assignees: GMT Gesellschaft für Medizinische Technik mbH; Waldemar Link GmbH & Co., both of Hamburg, Japan

[21] Appl. No.: 771,489

[22] Filed: Sep. 3, 1985

Related U.S. Application Data

[63] Continuation of Ser. No. 414,441, Sep. 2, 1982, abandoned.

[51] Int. Cl.⁴ ............................................... A61F 2/36
[52] U.S. Cl. ..................................................... 623/23
[58] Field of Search ....................... 623/16, 18, 19, 20, 623/21, 22, 23; 128/92 D, 92 C, 92 B, 92 CA

[56] References Cited

U.S. PATENT DOCUMENTS

| | | | |
|---|---|---|---|
| 3,748,662 | 7/1973 | Helfet | 128/92 C |
| 3,852,831 | 12/1974 | Dee | 128/92 C |
| 3,879,767 | 4/1975 | Stubstad | 128/92 C |
| 3,979,778 | 9/1976 | Stroot | 128/92 C |
| 4,156,944 | 6/1979 | Schreiber et al. | 128/92 C |
| 4,280,231 | 7/1981 | Swanson | 128/92 C |

Primary Examiner—Richard J. Apley
Assistant Examiner—David J. Isabella
Attorney, Agent, or Firm—Peter K. Kontler

[57] ABSTRACT

A prosthesis which is particularly well-suited for use in the region of the hip joint has a shaft which carries a bearing at one end. The bearing has a rim at its junction with the shaft. The end of the bearing opposite the rim has a saddle-shaped portion including a pair of protrusions which flank a depression. The depression has a pair of bearing surfaces separated by a protuberance which is formed in the depression and extends from one of the protrusions to the other. The prosthesis is installed at a hip joint by inserting the shaft into the end of the femur nearest the pelvis. The shaft is pushed into the femur until the rim on the bearing contacts the end of the femur. One of the protrusions is passed through an opening in the wall of the pelvis so that the wall is received in the depression of the bearing. The wall is contoured so as to conform to the shape of the depression and the protuberance therein and rests on the surface of the protuberance as well as the bearing surfaces of the depression. When the prosthesis has been installed in this manner, relative pivotal movement of the femur and the pelvis is possible. The prosthesis makes it possible to obtain relative pivotal movement of the femur and the pelvis even when the pelvis has been damaged or has deteriorated to such an extent that the natural socket can neither be repaired nor replaced.

28 Claims, 5 Drawing Figures

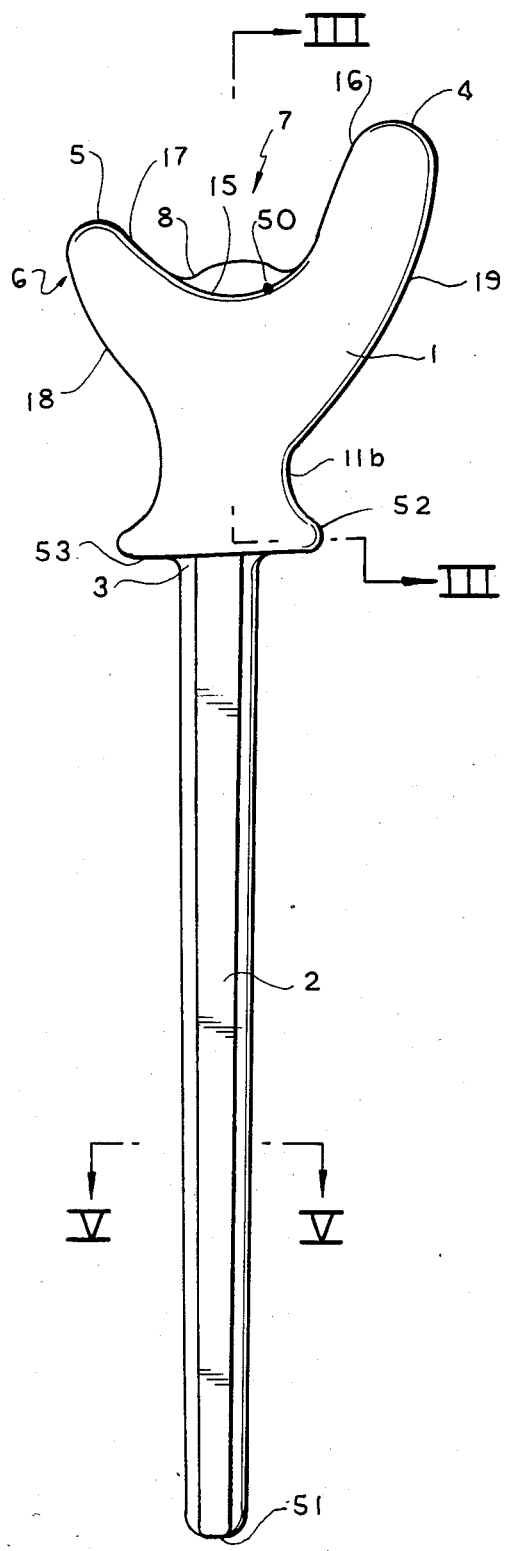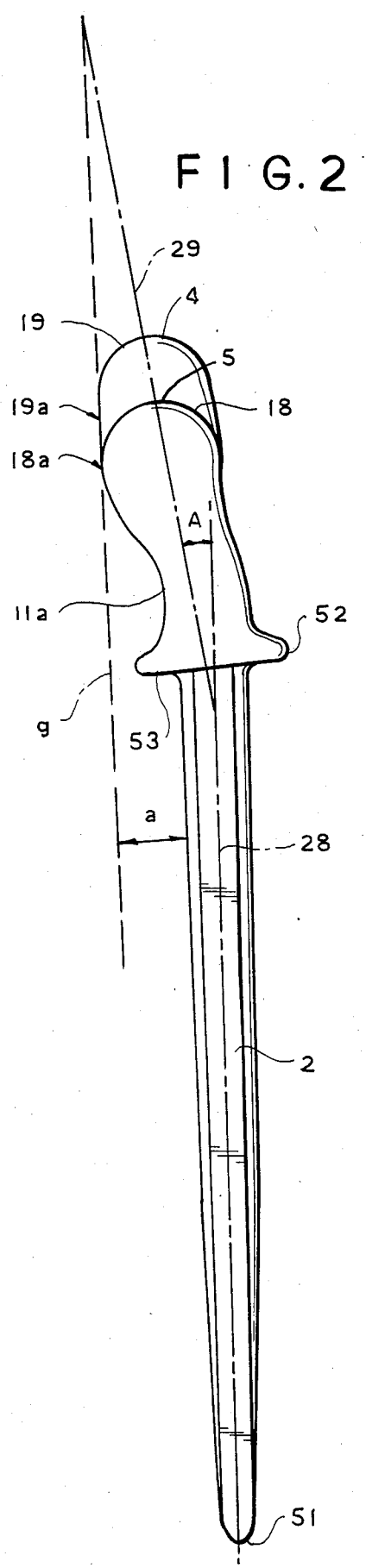

FIG. 3
FIG. 4
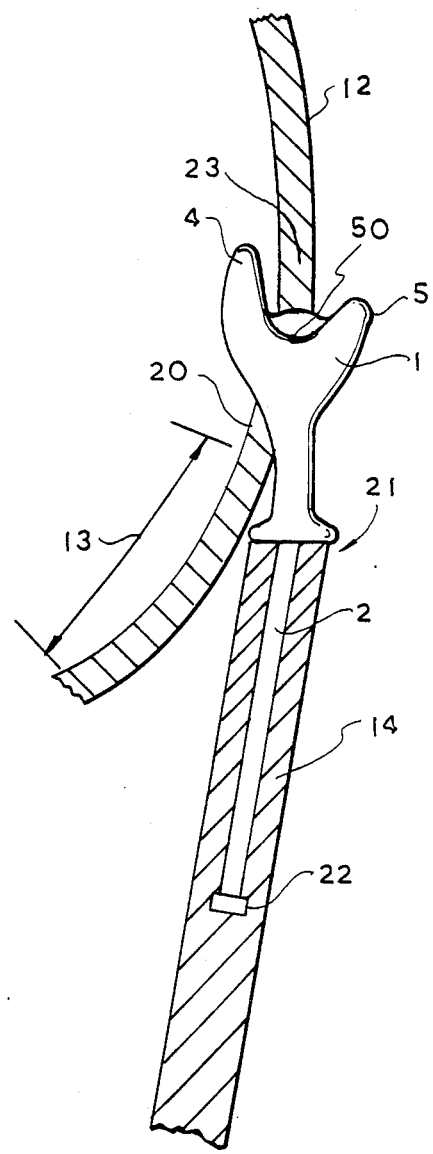
FIG. 5
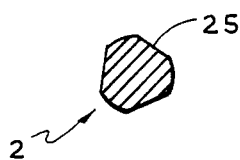

PROSTHESIS

This application is a continuation, of application Ser. No. 414,441, filed Sept. 2, 1982, now abandoned.

BACKGROUND OF THE INVENTION

The invention relates generally to a prosthesis.

More particularly, the invention relates to an internal prosthesis for use when a joint loses the ability to perform pivotal movements.

The ability of a joint to perform rotational and/or pivotal movements is sometimes lost because of damage to or deterioration of the socket. In certain situations, the ability of the joint to perform such movements have be restored by implanting a bearing in the bone having the affected socket. The bearing then assumes the function of the socket. In many cases, however, deterioration of the bone prevents implantation of a bearing. For example, deterioration of the pelvis in the region of the hip joint may make it impossible to implant a standardized or specialized artificial socket or to reconstruct the natural socket by means of spongiosaplasty or synthetic osteological compounds. The installation of an internal prosthesis may not be possible when the natural socket cannot be reconstructed or replaced by an artificial socket.

In such situations, reconstruction operations such as, for instance, resection arthroplasty, may be performed. However, operations of this type do not yield entirely satisfactory results.

In the case of a hip joint, the so-called girdlestoneplasty may be used when the natural socket cannot be replaced or reconstructed. Here, the femur is pressed against the pelvis by means of straps. With this type of connection, positive engagement between the femur and the pelvis is achieved in a horizontal plane but not in the direction of force transmission between the pelvis and the femur. Consequently, undesired relative displacement of the pelvis and the femur may occur with attendant instability and pain.

OBJECTS AND SUMMARY OF THE INVENTION

It is an object of the invention to provide a prosthesis which makes it possible to achieve pivotal movement at a joint even when the socket has deteriorated.

Another object of the invention is to provide a prosthesis which makes it possible to reliably connect two members of the anatomy which normally pivot relative to one another.

An additional object of the invention is to provide a prosthesis which is capable of maintaining two members of the anatomy in a predetermined relative orientation.

A further object of the invention is to provide a prosthesis which enables forces to be transmitted from one member of the anatomy to another without affecting the relative orientation of the members.

A concomitant object of the invention is to provide a prosthesis which is capable of reducing discomfort for the user.

It is also an object of the invention to provide a prosthesis which enables instability to be reduced.

Yet another object of the invention is to provide a prosthesis which may be implanted in one member of the anatomy in such a manner as to permit pivotal movement of such member relative to an adjacent member of the anatomy while maintaining the two members in a predetermined relative orientation even during the transmission of forces between the members.

The preceding objects, as well as others which will become apparent as the description proceeds, are achieved by the invention.

One aspect of the invention resides in a prosthesis comprising an anchoring element designed to be secured to a first member of the anatomy, e.g. a bone, which normally pivots relative to an adjacent second member of the anatomy, e.g. a bone. A bearing element is provided on the anchoring element and is designed to directly engage the second member of the anatomy in such a manner as to permit pivotal movement of this member relative to the first member of the anatomy.

The anchoring element may be in the form of a shaft which is designed to be embedded or implanted in a bone. The bearing element may be located at one longitudinal end of the shaft while the other longitudinal end may be designed to be situated inside the bone.

By forming appropriate cooperating bearing surfaces on the bearing element and the adjacent member of the anatomy, the latter may be brought into positive engagement with the bearing element. Such positive engagement prevents undesired relative displacement of the bearing element and the adjacent member of the anatomy under load. Accordingly, the characteristics achieved after installation of the prosthesis according to the invention will remain almost unchanged.

The cooperating bearing surfaces on the bearing element and the adjacent member of the anatomy may be designed in such a manner that little wear occurs during use. The changes of either the bearing element or the adjacent member becoming worn out are then minimal.

In the event that the bearing element engages a bone, the latter may undergo an increase in density under load. This has the advantage of stabilizing the bone.

A favorable embodiment of the invention contemplates for the bearing element to engage a bone and for the bearing surface on the bone to be constituted by an edge of the latter. An experienced surgeon will have no trouble in ascertaining which location of the edge of a bone is best suited to cooperate with the bearing element. The edge of the bone may be shaped in such a manner that no difficulties arise when the edge cooperates with the bearing surface on the bearing element. Furthermore, the edge of the bone may be formed so that even large forces may be transmitted via such edge.

The novel features which are considered as characteristic of the invention are set forth in particular in the appended claims. The improved prosthesis itself, however, both as to its construction and its mode of operation, together with additional features and advantages thereof, will be best understood upon perusal of the following detailed description of certain specific embodiments with reference to the accompanying drawings.

BRIEF DESCRIPTION OF THE DRAWINGS

FIG. 1 is a side view of an internal prosthesis according to the invention;

FIG. 2 is a front view of the prosthesis of FIG. 1;

FIG. 3 is a cross-sectional view in the direction of the arrows III—III of FIG. 1;

FIG. 4 is a cross-sectional view through a pelvis and a femur illustrating a manner of pivotally connecting the pelvis and the femur via the prosthesis of FIG. 1; and FIG. 4 is a cross-sectional view in the direction of the arrows V—V of FIG. 1.

DESCRIPTION OF THE PREFERRED EMBODIMENTS

The prosthesis of the invention is particularly well-suited for internal use in the region of a joint where the natural socket has deteriorated or has been damaged to such an extent that it can no longer pivotally support a bone and is incapable of being reconstructed or replaced with an artificial socket. The prosthesis according to the invention enables a pivotal connection to be established between the socket and the adjacent bone despite such deterioration or damage. For ease of understanding, and not by way of limitation, the following description will refer to the establishment of a pivotal connection between a femur and a pelvis.

Referring to FIGS. 1 and 2, the prosthesis in accordance with the invention includes a shaft or anchoring element 2 and a bearing or bearing element 1. The shaft 2 is designed to be embedded in a femur 14 shown in FIG. 4 while the bearing 1 is designed to directly engage a pelvis 12 also shown in FIG. 4.

The shaft 2 has a mounting end 3 and an insertion end 51. The bearing 1 is fixedly secured to the mounting end 3. The insertion end 51 is designed to be inserted into the femur 14.

The bearing 1 has a rim 52 in the region of the junction with the shaft 2. The rim 52 projects radially outward from the shaft 2 so that the diameter or width of the rim 52 is greater than the diameter or width of the shaft 2. The lower surface 53 of the rim 52, which faces the shaft 2, constitutes an abutment surface which abuts the upper end 21 of the femur 14 when the shaft 2 is embedded in the femur 14.

The bearing 1 is provided with a saddle-shaped portion 6 at the end thereof remote from the rim 52. The saddle-shaped portion 6 includes a pair of opposed protrusions 4 and 5 which flank and are connected by a depression 7. The protrusions 4 and 5 extend generally in a direction away from the shaft 2. In the illustrated embodiment, the length of the protrusion 4 exceeds that of the protrusion 5. However, it is possible for the protrusions 4 and 5 to be of equal length.

A protuberance 8 having a generally part-spherical configuration is located in the depression 7. The protuberance 8 extends from the protrusion 4 to the protrusion 5. The surface of the protuberance 8 flattens as it approaches the protrusions 4 and 5 and becomes essentially flat in the regions of the latter.

The protrusions 4 and 5 lie on a straight line with the depression 7 and the protuberance 8. In a direction generally perpendicular to this line, the surface of the protuberance 8 merges into bottom surfaces 15 of the depression 7. As illustrated in FIG. 3, one such bottom surface 15 is located on either side of the protuberance 8 as considered in a direction substantially normal to the line of the protrusions 4 and 5. The bottom surfaces 15 of the depression 7 constitute bearing surfaces as will be described more fully below.

The bearing surfaces 15 are part-circular and extend from the protrusion 4 to the protrusion 5. As most clearly illustrated in FIG. 1, the protrusion 4 has an internal surface 16 which faces the protrusion 5 while the latter has an internal surface 17 which faces the protrusion 4. The internal surfaces 16 and 17 meet the bearing surfaces 15 tangentially, that is, the internal surfaces 16 and 17 merge smoothly into the bearing surfaces 15.

As most clearly seen in FIG. 2, the protrusions 4 and 5 are inclined with respect to the shaft 2. In other words, the protrusions 4 and 4 are so arranged that a plane 29 defined by the longitudinal center lines of the protrusions 4 and 5 makes an angle "A" with the longitudinal axis 28 of the shaft 2. The angle "A" may, for example, be in the range of 30 degrees.

The bearing 1 has an external cavity or recess made up of at least two portions 11a and 11b. The cavity portion 11a extends in a direction which is generally parallel to the line on which the protrusions 4 and 5 are located while the central plane of the cavity portion 11a, which is not illustrated, is transverse to the plane 29 defined by the center lines of the protrusions 4 and 5, i.e. the central plane of the cavity portion 11a is parallel to the plane of the paper when considering FIG. 2. On the other hand, the cavity portion 11b extends transversely of the line on which the protrusions 4 and 5 are located. The central plane of the cavity portion 11b coincides with the plane 29 defined by the center lines of the protrusions 4 and 5.

The cavity 11a, 11b is located adjacent to the rim 52, that is, in the region of the junction between the bearing 1 and the shaft 2. The cavity 11a, 11b is designed so as to conform to the configuration of the pelvis 12. With reference to FIG. 4, it may be seen that the pelvis 12 has an arcuate section 13 which may be considered to constitute an arch or a bulge. The arcuate section 13 approaches the bearing 1 from below and the upper end of the arcuate section 13 is located in the vicinity of the bearing 1. The cavity 11a, 11b takes account of the fact that the prosthesis must be spaced from the pelvis 12 by an amount sufficient to permit unrestricted relative pivotal movement of the pelvis 12 and the femur 14. In other words, the cavity 11a, 11b makes it possible for the pelvis 12 and the femur 14 to undergo the required amount of relative pivotal movement without contact between the femur 14 and the arcuate section 13 of the pelvis 12 or between the prosthesis and the arcuate section 13. The cavity 11a, 11b must be designed in such a manner than, when the bearing 1 engages the pelvis 12, the shaft 2 projects into the femur 14 along the natural direction of the latter.

The protrusion 4 has an external surface 19 which bounds the same externally while the protrusion 5 is externally bounded by an external surface 18. The external surfaces 18 and 19 continue down to the rim 52 which circumscribes the lower end of the bearing 1. On the side of the bearing 1 with the cavity portion 11a, the external surfaces 18 and 19 extend to the rim 52 via the cavity portion 11a located between the rim 52 and the protrusions 4 and 5. The external surface 19 also passes through the cavity portion 11b located between the protrusion 4 and the rim 52. The contours of the external surfaces 18 and 19 conform approximately to the force pattern which is generated in the bearing 1 under load.

On the side of the bearing 1 having the cavity portion 11a, the external surface 18 of the protrusion 5 has a portion 18a which is located farther from the longitudinal axis 28 of the shaft 2 than the remainder of the external surface 18. Similarly, the external surface 19 of the protrusion 4 has a portion 19a which is displaced from the longitudinal axis 28 of the shaft 2 by a larger amount than the remaining portions of the external surface 19. This is most clearly illustrated in FIG. 2. The surface portions 18a and 19a are located in a common plane 9 which, in the illustrated embodiment, is parallel to the longitudinal axis 28 of the shaft 2. The plane 9 bounds the cavity 11a, 11b on the side of the bearing 1 having the cavity portion 11a and is spaced from the longitudinal axis 28 of the shaft 2 by a distance "a" equal to the depth of the cavity 11a, 11b. It will be observed that the plane 9 intersects the central plane 29 of the cavity portion 11b and the protrusions 4, 5.

The free upper ends of the protrusions 4 and 5 are rounded in a direction transverse to the plane 9. Preferably, the free ends of the protrusions 4 and 5 are rounded so as to be part-circular. Instead of rounding the free ends of the protrusions 4 and 5 only in a direction transverse to the plane 9, it is possible to round these ends so that they are part-spherical.

The prosthesis is installed as follows:

The shaft 2 is inserted into the femur 14 by passing the insertion end 51 of the shaft 2 through the upper end 21 of the femur 14. The shaft 2 is pushed down into the femur 14 until the abutment end 53 of the rim 52 lies against the upper end 21 of the femur 14. Abutment of the rim 52 against the upper end 21 of the femur 14 assures that forces can be transmitted between the bearing 1 and the femur 14 without difficulty. In order to properly position and guide the shaft 2 in the femur 14, the insertion end 51 of the shaft 2 may be provided with a star-shaped guide element 22. The projections on the guide element 22 insure that the shaft 2 travels along the desired path until it reaches its final position.

The shaft 2 is firmly anchored in the femur 14. This is advantageously accomplished using an appropriate cement for bones.

After the shaft 2 has been anchored in the femur 14, one of the protrusions 4, 5 is inserted into an opening 20 provided in the pelvis 12. The opening 20 may be mechanically formed in the pelvis 12 or may have been previously present. Frequently, an opening is formed in the pelvis 12 as a result of damage to or deterioration of the same and such an opening may serve as the opening 20. In any event, the opening 20 should be located in a region of the pelvis 12 which is sufficiently strong to withstand the forces which are transmitted between the femur 14 and the pelvis 12.

The opening 20 is bounded from above by a section 23 of the pelvis 12. When the protrusion 4 or 5 is passed through the opening 20, the section 23 is received between the protrusions 4 and 5, that is, one of the protrusions 4, 5 is located inside the pelvis 12 while the other of the protrusions 4, 5 is located outside of the pelvis 12. The pelvic section 23 has a bearing surface which is shaped so as to correspond to the configuration of the depression 7 and the protuberance 8. The bearing surface of the pelvic section 23 engages the surface of the protuberance 8 as well as the bearing surfaces 15 of the depression 7. The prosthesis is designed in such a manner that the bearing surface of the pelvic section 23 engages the bearing surfaces 15 at areas 50 located at the deepest part of the depression 7, i.e. the depression 7 has its greatest depth at the areas 50. The areas 50 are located to one side of the longitudinal axis 28 of the shaft 2 and nearer the protrusion 4 or 5 inside the pelvis 12 than the protrusion 4 or 5 outside the pelvis 12. The areas 50 define a line which extends transversely of the plane 9 and the line on which the protrusions 4, 5 are located. Accordingly, the pelvic section 23 and its bearing surface extend transversely of the plane 9 and the line on which the protrusions 4, 5 are situated.

In the illustrated embodiment, the bearing surface of the pelvic section 23 is defined by an edge of the latter which is more or less in line contact with the bearing surfaces 15 and the surface of the protuberance 8. An experienced surgeon can shape the edge so as to maximize the area with which the pelvic section 23 rests upon the protuberance 8 and the bearing surfaces 15.

It is preferred for the diameter of the bearing surfaces 15 to be approximately equal to the thickness of the pelvic section 23.

The protrusions 4, 5 are designed to prevent disengagement of the bearing 1 from the pelvis 12. The longer protrusion 4 is especially well-suited for this purpose and for this reason is advantageously placed at the position where there is the greatest likelihood of the bearing 1 moving out of engagement with the pelvis 12. Generally, the longer protrusion 4 is passed through the opening 20 as illustrated in FIG. 4. The deepest areas 50 of the depression 7 are then located nearer the protrusion 4 than the protrusion 5. However, it is possible to insert the shorter protrusion 5 rather than the longer protrusion 4 into the opening 20. In this case, the deepest areas 50 of the depression 7 will be situated nearer the protrusion 5 than the protrusion 4.

It will be observed that the one of the protrusions 4, 5 to be passed through the opening 20 must be determined in advance. The reason is that the prosthesis must be designed accordingly so that the shaft 2 extends in the natural direction of the femur 14 when the selected protrusion 4 or 5 is located inside the pelvis 12.

It is further necessary to design the bearing 1 so that it conforms to the contour of the pelvis 12 in the region of the opening 20. The depth of the cavity 11a, 11b must be selected in such a manner that relative pivotal movement of the pelvis 12 and femur 14 can occur without abutment of the femur 14 or the bearing 1 against the pelvis 12. The distance between the rim 52 and the saddle-shaped portion 6, or the length of the cavity 11a, 11b as considered in the longitudinal direction of the prosthesis, is determined by the distance between the pelvic section 23 and the upper end 21 of the femur 14.

The angle between the planes 9 and 29 is also selected in dependence upon the contour of the pelvis 12 in the vicinity of the opening 20 and may be varied as desired to suit the particular conditions. It is even possible for the planes 9 and 29 to be parallel to one another.

The shaft 2 may have any desired cross section. For example, the cross section of the shaft 2 may be circular. It is also possible for the shaft 2 to have a polygonal cross section as illustrated in FIG. 5 where the shaft 2 is provided with three planar surfaces 25 uniformly distributed about its circumference. A polygonal cross section is more effective than a circular cross section in preventing rotation of the shaft 2 within the femur 14. The shaft 2 may have a uniform cross section throughout substantially its entire length or may taper inwardly throughout substantially its entire length in a direction from the mounting end 3 to the insertion end 51. It is also possible for the shaft 2 to have a portion of constant cross section adjacent to the bearing 1 and for the remainder of the shaft 2 to taper inwardly in a direction towards the insertion end 51. A tapered configuration has the advantage of facilitating insertion of the shaft 2 into the femur 14. By way of example, the shaft 2 may be cylindrical along any part thereof having a constant cross section and conical along any part thereof which tapers.

The prosthesis may be composed of a chromium-cobalt-molybdenum alloy.

The prosthesis in accordance with the invention may constitute part of an entire prosthetic system for the femur. Thus, the prosthesis may be used when there has been a partial proximal femur replacement or a total femur replacement.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. An articular prosthesis for implanting in a region of a joint, where a natural joint socket has deteriorated to such an extent that it can no longer pivotally support a bone and where the natural joint socket is incapable of being replaced with an artificial joint socket, comprising: an elongated anchoring element sized so as to be secured in an interamedullary canal and formed at one end of said anchoring element is a substantially U-shape bearing element; said bearing element having a pair of protrusions forming leg portions of said U-shape and a base portion, disposed between said protrusions, forming a bearing surface; and said bearing surface being sized generally to cooperate with an edge face of a pelvis bone at a location other than the original joint between the pelvis and the femur and wherein said bearing surface of said base portion directly engages the edge face thereby permitting functional pivotal movement between the pelvis and femur.

2. The prosthesis of claim 1, wherein said anchoring element comprises a shaft.

3. The prosthesis of claim 1, wherein said protrusions are of unequal length.

4. The prosthesis of claim 1, said anchoring element being elongated and having a longitudinal axis; and wherein said bearing element is provided with a cavity which at least partly circumscribes said bearing element and defines a clearance permitting relative pivotal movement of the femur and pelvis, said protrusions having respective external surface portions located in a common plane bounding said cavity, and said common plane substantially paralleling said axis and being spaced from said anchoring element by a distance substantially equal to the depth of said cavity.

5. The prosthesis of claim 1, wherein said anchoring element has a smaller cross section than said bearing element through.

6. The prosthesis of claim 1, said bearing element having a first portion which is designed to abut the femur and a second portion which includes said protrusions and said bearing surface, the distance between said first and second portions being determined by the distance between the femur and the edge face of the pelvis.

7. The prosthesis of claim 1, wherein said anchoring element has a circular cross section.

8. The prosthesis of claim 1, wherein said anchoring element has a polygonal cross section.

9. The prosthesis of claim 1, wherein said anchoring element has an insertion end remote from said bearing element and said insertion end is provided with a guide portion to facilitate insertion of said anchoring element into the femur member.

10. The prosthesis of claim 1, wherein said anchoring element is cylindrical.

11. The prosthesis of claim 1, wherein said anchoring element includes a tapered portion which decreases in cross section with increasing distance from said bearing element.

12. The prosthesis of claim 11, wherein said anchoring element further includes a cylindrical portion between said tapered portion and said bearing element.

13. The prosthesis of claim 11, wherein said tapered portion is conical.

14. The prosthesis of claim 1, wherein one protrusion of said bearing element is designed to project through an opening in the pelvis and said bearing surface is designed to pivotally engage that edge face of the pelvis which bounds the opening from above.

15. The prosthesis of claim 1, wherein said bearing element is provided with a cavity which at least partly circumscribes said bearing element and defines a clearance permitting relative pivotal movement of the femur and members.

16. The prosthesis of claim 1, wherein said anchoring element is elongated and has a pair of longitudinally spaced ends, said bearing element being mounted at one of said ends.

17. The prosthesis of claim 1, wherein said bearing element is provided with a depression and at least part of said bearing surface is located in said depression.

18. The prosthesis of claim 17, wherein said protrusions and said depression are arranged along a predetermined line which extends transverse to said bearing surface.

19. The prosthesis of claim 17, said protrusions having free ends remote from said depression; and wherein said free ends are rounded.

20. The prosthesis of claim 19, said protrusions and depression being arranged along a predetermined line; and wherein said free ends are rounded in a direction transverse to said predetermined line.

21. The prosthesis of claim 17, said protrusions and depression being arranged along a predetermined line; and wherein said bearing element is provided with a cavity which is at least partly circumscribes said bearing element and defines a clearance permitting relative pivotal movement of the femur and pelvis, at least a portion of said cavity extending transversely of said predetermined line.

22. The prosthesis of claim 17, wherein said bearing surface comprises a protuberance which is arranged in said depression and said protuberance is provided with part of said bearing surface.

23. The prosthesis of claim 22, wherein said part of said bearing surface which is provided on said protuberance is shaped so as to provide for a linear contact area with the pelvis during pivotal motion.

24. The prosthesis of claim 17, wherein said depression has a cross section substantially in the form of a circular arc.

25. The prosthesis of claim 17, wherein said depression has its greatest depth at a location near one of said protrusions.

26. The prosthesis of claim 25, said anchoring element being elongated and having a central longitudinal axis which passes between said protrusions; and wherein said depression is spaced from said axis and arranged on a side remote from said other protrusion.

27. The prosthesis of claim 25, wherein said one protrusion is longer than said other protrusion.

28. The prosthesis of claim 17, wherein said part of said bearing surface is substantially in the form of a circular arc and merges smoothly into said protrusions.

* * * * *

UNITED STATES PATENT AND TRADEMARK OFFICE
CERTIFICATE OF CORRECTION

PATENT NO. : 4,645,507
DATED : February 24, 1987
INVENTOR(S) : Eckart ENGELBRECHT et al.

It is certified that error appears in the above-identified patent and that said Letters Patent are hereby corrected as shown below:

| | |
|---|---|
| Foremost Page [73] | - "Japan" should read --Federal Republic Germany--. |
| Col. 1, line 15 | - "have" should read --may--. |
| Col. 2, line 32 | - "changes" should read --chances--. |
| Col. 3, line 1 | - "FIG. 4" should read --FIG. 5--. |
| Col. 3, line 20 | - before the first "bearing" insert --substantially V-shaped--. |
| Col. 4, line 5 | - the second "4" should read --5--. |
| Col. 7, line 54 | - after "element" insert --.--. |
| Col. 7, line 55 | - cancel "through". |
| Col. 7, line 70 | - after "femur" insert --.-- and delete "member." |
| Col. 8, line 21 | - "members." should read --pelvis.--. |
| Col. 8, line 43 | - delete "is". |
| Col. 8, after the last claim | - add the following claim: --29. The prosthesis of claim 19, wherein said free ends are substantially in the form of circular arcs.--. |

On the title page "28" Claims" should read -- 29 Claims --.

Signed and Sealed this

First Day of September, 1987

Attest:

DONALD J. QUIGG

Attesting Officer

Commissioner of Patents and Trademarks